United States Patent [19]

McFarlane

[11] Patent Number: 4,509,946
[45] Date of Patent: Apr. 9, 1985

[54] FLOW CONTROL DEVICE

[76] Inventor: Richard H. McFarlane, 2571 Kaneville Rd., Geneva, Ill. 60134

[21] Appl. No.: 421,989

[22] Filed: Sep. 23, 1982

[51] Int. Cl.³ .......................... A61M 5/00; A61B 5/02
[52] U.S. Cl. .................................... 604/246; 128/673; 604/30; 251/117
[58] Field of Search .................... 128/672-673, 128/675, 748; 604/30, 32-34, 246; 251/117; 137/238

[56] References Cited

U.S. PATENT DOCUMENTS

| | | | |
|---|---|---|---|
| 3,675,891 | 7/1972 | Reynolds et al. | 128/673 X |
| 4,192,303 | 3/1980 | Young et al. | 251/117 X |
| 4,245,636 | 1/1981 | Sparks et al. | 251/117 X |
| 4,278,083 | 7/1981 | Young et al. | 251/117 X |
| 4,291,702 | 9/1981 | Cole et al. | 128/673 X |
| 4,300,571 | 11/1981 | Waldbillig | 128/673 |
| 4,341,224 | 7/1982 | Stevens | 128/673 X |
| 4,373,524 | 2/1983 | Leibinsohn | 251/117 X |
| 4,381,591 | 5/1983 | Barger et al. | 604/30 X |
| 4,410,164 | 10/1983 | Kamen | 604/34 X |
| 4,414,999 | 11/1983 | Basta | 251/117 X |

Primary Examiner—Lee S. Cohen
Assistant Examiner—Angela D. Sykes
Attorney, Agent, or Firm—John Cyril Malloy

[57] ABSTRACT

A flow control device designed to be used in combination with a catheter system itself designed for monitoring circulatory status including venous and arterial pressure where the subject flow control device provides a continuous flow of infusion fluid throughout the catheter system to prevent occlusion of the system resulting in inaccurate monitoring. The flow control device further has the ability to flush the entire system rapidly by selectively passing a larger quantity of infusion fluid throughout the catheter system when desired.

9 Claims, 5 Drawing Figures

U.S. Patent        Apr. 9, 1985        4,509,946
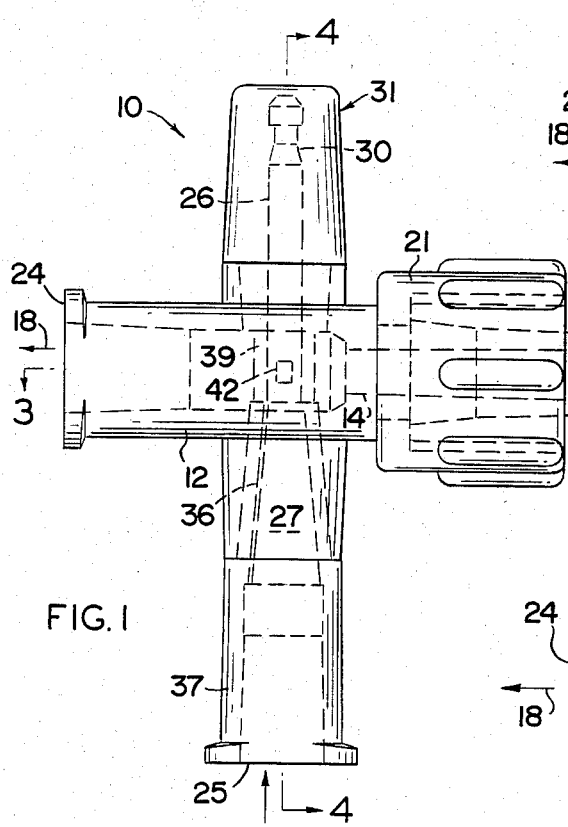
FIG. 1
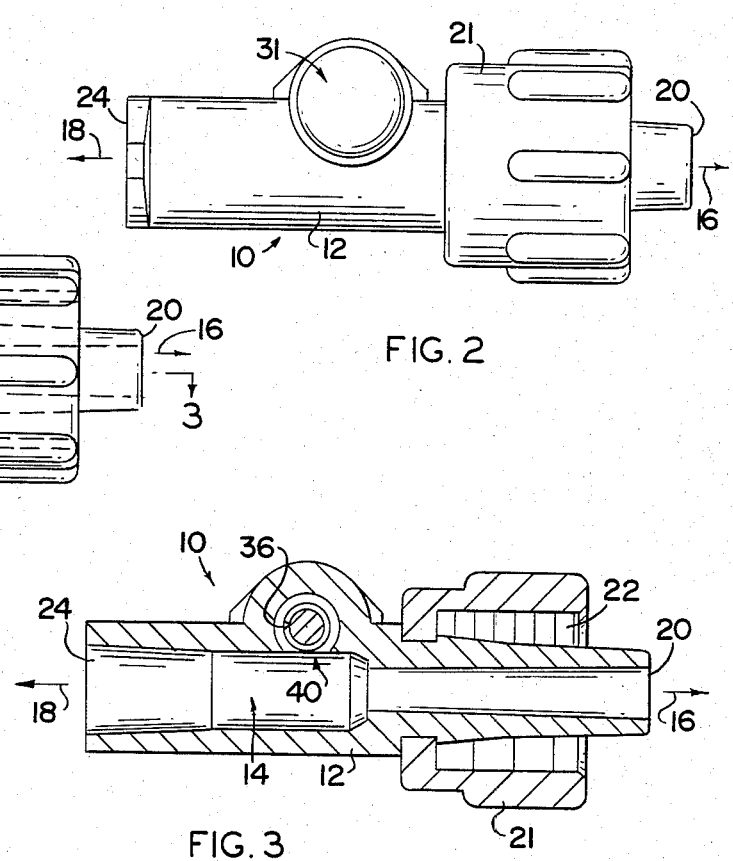
FIG. 2
FIG. 3
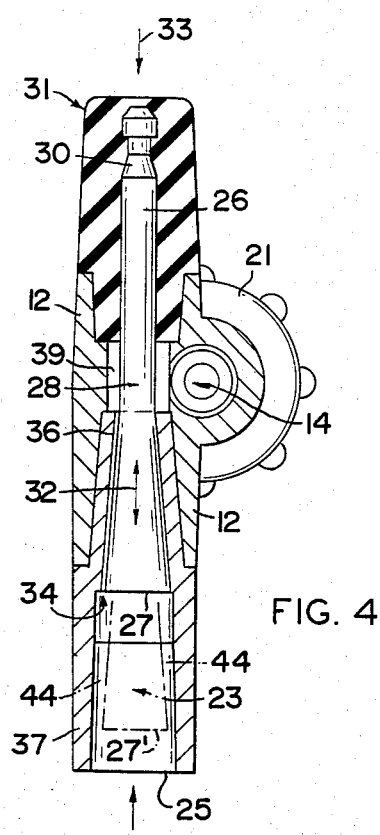
FIG. 4
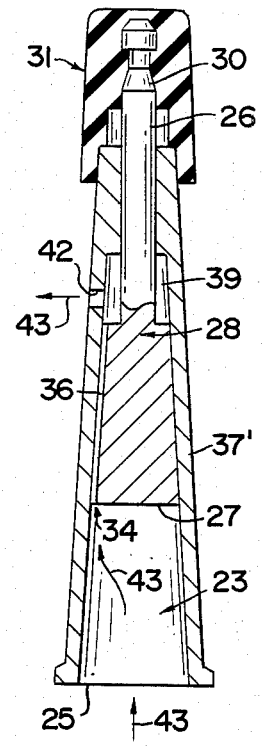
FIG. 5

FLOW CONTROL DEVICE

BACKGROUND OF THE INVENTION

1. Field of the Invention

This invention relates to a flow control device directed to the continous flow of a saline solution or like infusion solution throughout an intravascular pressure monitoring catheter system wherein the device has the capabilities of thoroughly flushing the system through the introduction of larger quantities of the infusion solution throughout the entire system.

2. Description of the Prior Art

The monitoring of intravascular pressure utilizing a catheter assembly is well recognized as standard procedure in modern medical facilities. Through the utilization of the above-noted prior art technique, it is possible to measure such various parameters as stroke volume, heart rate, cardiac output, duration of systole, and systolic, diastolic and mean pressures.

As pointed out in U.S. Pat. No. 3,675,891 to Reynolds, et al., the efficient operation of this well recognized system requires a continuous flushing of the entire catheter structure. This flushing requirement is needed to prevent the blockage of the catheter device caused by blood clotting. This is especially true when, as is common in most monitoring situations, the catheter must remain in place for long periods of time.

However, various flow regulating devices attempting to accomplish such flushing requirements in the aforementioned catheter monitoring systems have encountered problems concerned with leakage as well as overly complex structures. Such problems have manifested themselves in a loss of accuracy of recording due to the existence of blood clots and otherwise thick or high viscosity blood forming and being maintained within the catheter system. The leakage, as present in prior art systems, allows a certain amount of the blood from the patient to enter the catheter tip causing the aforementioned blockage problems because of diffusion of the blood. This diffusion allows further penetration into the catheter and the final result of occlusion somewhere in the system.

With a standard continuous flush or flow device only a minuscule amount of infusion solution, such as saline solution, may be continuously introduced to prevent harm to the patient. This extremely slow fluid flow would take many hours to enter the entire system when a cleaning or flushing of the system is desired. Therefore, there is a need in the art for a flow control device capable of maintaining the regulated and predetermined amount of minimum flow of infusion solution for the purpose of preventing occlusion while at the same time having the capabilities of flushing the entire system in a rapid time saving manner.

The above-noted U.S. Patent to Reynolds, et al. discloses a device capable of operatively performing the continuous and intermittent flushing procedures. However, a review of the devices currently available and presently existing in the prior art reveals the need for a structure of simple design, reliable performance and adaptability for existing intravascular catheter monitoring systems.

SUMMARY OF THE INVENTION

The instant invention is directed toward a flow control device which, is described primarily for use in combination with a catheter system for monitoring intravascular status. More specifically, the present invention is used to continuously supply a flushing solution or an infusion solution such as saline or the like throughout a catheter system for the purpose of preventing blocking of the system due to the formation of blood clots. It is readily apparent that the blocking or occlusion of such a catheter type system would result in a reduction of integrity of the monitored parameters especially when the system is utilized for the monitoring of such pressure over a long period of time. It will be readily apparent however that while the subject invention is described particularly in combination with the type of catheter system described above, it can readily be adapted to other type systems for the purpose of governing flow throughout any other type system.

More particularly, the structure of the present invention comprises a housing means incorporating a first flow channel which allows open fluid communication between a patient and a pressure transducer or other type of monitoring apparatus. The first flow channel may therefore be connected to the patient by conventional tubing attached to one end of the first flow channel while the other end leads directly to the aforementioned monitoring apparatus. A second flow channel is also formed within the housing in fluid communication with the first flow channel wherein the free end of the second flow channel is interconnected to a supplemental source of infusion fluid such as saline solution or the like.

The fluid communication and the flow of fluid from the second flow channel to the first flow channel is accomplished either through a continuous path of fluid flow or through an intermittent path of fluid flow. As will be explained in greater detail hereinafter, the continuous path of fluid flow is primarily defined by a finite groove means formed on the outer surface of a flow regulator plug element or on the interior surface of the housing, the plug being movably mounted to be reciprocally positioned along a longitudinal axis on the interior of the second flow channel. The illustrated groove means is specifically disposed, structured and dimensioned to allow a continuous predetermined amount of fluid flow to pass from the supplemental saline solution source, through the second flow channel, and past the flow regulator means plug element by means of passage through the finite groove means. Flow continues through various cavity chambers leading eventually to the first flow channel and therefore throughout the remainder of the catheter system.

The disposition of the plug element in its closed position effectively seals off all fluid flow from the second flow channel to the first flow channel except through the groove means. This causes a predetermined small amount, in the range of 2 cc. to 6 cc. as desired, to constantly flow from the source of infusion solution throughout the entire system for the purpose of preventing blocking or occlusion of the system.

In that such a small amount is continuously passing through the groove means defining the continuous path of fluid flow, it is obvious that flushing or cleaning of the entire system would require larger amounts of saline solution to pass through the system and would take many hours. Therefore, there is a need for providing a flushing surge of saline solution to enter the entire catheter system for the purpose of initial purging or flushing. This may be required prior to the system being put in operation. To accomplish such flushing procedure, the structure of the subject flow control device provides an intermittent path of fluid flow from the second flow channel to the first flow channel. Such second, intermittent path of fluid flow comprises the positioning of the plug element into a depressed disposition along a longitudinal axis on the interior of the second flow channel. This causes a spacing of the major or body portion of the plug element from the interior surface of the second flow channel. This in turn greatly enlarges the path of travel which the saline solution may take when passing from the second flow channel, beyond and about the exterior surface of the plug element and into the first flow channel for rapid dispersement throughout the entire catheter system.

With reference to specific structural features of the drawing which will be described in greater detail hereinafter, it can readily be seen that the greater dimensions of the intermittent path of fluid flow causes a much greater amount of fluid to pass therealong when the intermittent path of fluid flow is open. This allows the entire system to be flushed prior to its initial operation and immediately prior to application of the catheter into the patient's vascular system. It is to be noted that the flushing can take place immediately prior to introduction of the catheter into the vascular system.

Selective or manual displacement of the plug element is readily accomplished due to the provision of a biasing means interconnected between the plug element and the housing. This interconnection is accomplished in such a fashion as to allow a manual or otherwise forced depression of the biasing means and plug element causing its displacement and movement along the longitudinal axis of the second flow channel on the interior thereof. Therefore, the continuous path of fluid flow is defined by mating engagement of the body portion of the plug element with the interior surface of the second flow channel. In such closed position, the only path of fluid flow throughout the second flow channel is along the continuous path of fluid flow defined by the groove means set forth above. When the greater amount of fluid flow is desired, as for flushing the entire catheter system, displacement of the plug element is selectively accomplished. This causes displacing of the outer surface of the plug element from the interior surface of the second flow channel, thereby opening the intermittent path of fluid flow which exists between the plug element and the interior surface of the second flow channel. As set forth above, since the dimension of the intermittent path of fluid flow is much greater, a much greater amount of fluid flow will pass from the second flow channel about and beyond the plug element into the first flow channel to accomplish flushing of the entire catheter system and cleaning in the sense that the flow will tend to dislodge any particulate matter plugging the continous flow path.

BRIEF DESCRIPTION OF THE DRAWINGS

For a fuller understanding of the nature of the present invention, reference should be had to the following detailed description taken in connection with the accompanying drawings, in which:

FIG. 1 is a front plan view of the flow control device of the present invention.

FIG. 2 is a top view of the structural embodiment of FIG. 1.

FIG. 3 is a sectional view showing the interior details of a first flow channel of the present invention.

FIG. 4 is a sectional view taken along line 4—4 of FIG. 2 showing the structural details on the interior of the second flow channel of the present invention.

FIG. 5 is a detailed sectional view of another embodiment showing structural details of the second flow channel and various paths of fluid flow leading therefrom to the remainder of the system.

Similar reference characters refer to similar parts throughout the several views of the drawings.

DETAILED DESCRIPTION OF THE PREFERRED EMBODIMENT

As shown in the figures, the flow control device of the present invention is generally indicated as 10 and comprises a housing means 12. The housing means includes (FIG. 3) a first flow channel 14 which is structured to provide open fluid communication between a patient indicated by directional arrow 16 and a monitoring device indicated by directional arrow 18. More specifically, one end of the first flow channel 14, as at 20, is connected by proper tubing and a fitting structure to a catheter device entering into the intravascular system of the patient being monitored. A connecting collar 21 having interior threads as at 22 may serve as a further attachment for properly connecting tubing of the catheter device leading to the patient. The opposite end of the first flow channel 14, as at 24, is connected directly to a monitoring system or apparatus (not shown). An open flow channel defined by the first flow channel 14 is thereby provided to allow the pulse waves in the circulatory system of the blood from the patient to be transmitted directly to the monitoring apparatus indicated by directional arrow 18. It is imperative in order to accomplish accurate monitoring that blocking or occlusion of the entire catheter system, including formation of blood clots throughout, be eliminated. Such blocking is prevented by means of the introduction of an infusion fluid into the first flow channel 14 and therefrom throughout the entire catheter system including up to and through the catheter tip.

With reference to FIGS. 4 and 5, the flow control device of the present invention further includes a second flow channel 23 formed within or connected directly to the housing 12 so as to be disposed in fluid communication with the first flow channel 14. One end as at 25 of second flow channel 23 is connected by proper tubing to a supplemental source of infusion fluid such as saline solution or the like. Such solution is directed to the interior of second flow channel 23. A flow regulator means 26 is movably mounted, at least in part, on the interior of the second flow channel 23. The flow regulator means 26 comprises a plug element having a body portion 27 and a stem portion 28. The distal end of the plug element as at 30 is disposed to project outwardly from the housing means 12 and is interconnected to a biasing means generally indicated as 31. The biasing means is formed of an elastic material and is interconnected between the distal end 30 of the plug element and the housing 12.

In a further embodiment the biasing means 31 is in the form of an elastic button which is disposed and structured to normally bias the plug element into its closed position as shown in FIG. 4. The plug element is reciprocally mounted to be displaced along the central longitudinal axis of the second flow channel as indicated by directional arrow 32. Force applied to the biasing means 31 as indicated by directional arrow 33 causes movement of the plug element towards end 25 of second flow channel 23. This in turn causes a spacing to occur between the exterior surface of the body portion 27 and the interior surface of the second flow channel 23. The manipulation of plug element will be hereinafter described relative to the establishment of a continuous flow channel and an intermittent flow channel.

In the illustrated preferred embodiment a continuous flow channel is generally indicated as 34 and is primarily defined by the existence of a groove means 36 integrally formed and recessed from the exterior surface of the body portion 27 of the plug element. It should be noted that groove means 36 could alternatively be provided in the housing and recessed inwardly from the interior surface of the second flow channel 23. Accordingly, when the plug element 26 (as shown in FIGS. 4 and 5) is in its closed position, fluid flow is prevented from passing the end 25 of second flow channel 23 into the first flow channel 14, except through the continuous path of fluid flow 34 defined by the groove means 36. In that this continuous path 34 is always open, a continuous flow of saline solution will always pass from the second flow channel 23 into the first flow channel 14 thereby preventing occlusion within the entire catheter system. However, since the groove means is specifically dimensioned to allow only a minimal amount of solution to pass therethrough (in the range of 2 cc. to 6 cc.) passage of large amounts of saline solution through the entire system for the purpose of flushing would obviously take many hours. Therefore, an intermittent path of fluid flow is also established on the interior of the second flow channel 23. This intermittent path is established when the flow regulator means 26 is depressed and displaced along the longitudinal axis of the second flow channel 23 into its "open" position indicated in greatly exaggerated fashion by broken lines as 27'. The actual stroke is about 0.050 inch. In such position, the body portion 27 is disengaged from its mating contact with the interior surface of the second flow channel 23. This allows much greater amounts of fluid to pass from the end 25 of second flow channel 23, about the outer surface of the body portion 27 of the plug element and into the first flow channel 14. Since much greater amounts of fluid are allowed to flow, the aforementioned flushing action will occur thereby flushing out the entire system prior to the insertion of the apparatus or during the insertion of the catheter system when the entire system is put on line for monitoring a patient.

Other structural features of the present invention include an integrally formed conduit member 37 being securely attached on the interior of the housing means 12 so as to place the second flow channel 23 in direct communication with a centrally located collection cavity 39.

With reference to FIG. 5, the cavity 39 is disposed in direct fluid communication with the first flow channel 14 generally at 40 (FIG. 3) through an aperture means 42 (FIGS. 1 and 5) contiguous and common to both the cavity 39 and the first flow channel 14. Directional arrow 43 shows the path of fluid flow into end 25 of the second flow channel 23, through the groove means 36 defining the continuous path of fluid flow and into the central cavity 39. As the fluid exits from cavity 39 through aperture 42, as at 43, it passes directly into the first flow channel 14 and throughout the entire system for the purposes of preventing occlusion as set forth above. When the flow regulator means 26 is disposed into its open position, the intermittent path of fluid flow is established between second flow channel 23 and cavity 39 by displacement of the outer surface of the body portion 27 from the interior surface of the second flow channel 23. Fluid is therefore allowed to flow about and over the major portion of the outer surface of the body portion 27 of plug 28 into the cavity 39. It is obvious since the intermittent path, herein indicated as 44 in broken line is much larger than the continuous path of fluid flow defined by groove means 36, a much greater amount of fluid will pass from the end 25 about the plug element into the central cavity 39 and eventually into the first flow channel 14.

After force has been removed from the biasing means 31, its resilient action due to it being made from elastic material, will normlly bias the plug 28 into its closed position as shown in solid lines in FIG. 4. Therefore, the continuous path of fluid flow will be re-established and remain the only means of open fluid communication between the second flow channel 23 and the first flow channel 14 through the central collection cavity 39.

With reference to the details of FIG. 5, the embodiment disclosed therein comprising a one-piece body structure in the form of conduit 37' forming a portion of the housing means rather than the conduit 37 (FIG. 4) being fitted into a receiving end of the housing means 12 as shown in FIG. 4.

What is claimed is:

1. A flow control device of the type primarily designed for use with an intravascular pressure monitoring catheter system, said device comprising:
   (a) a housing including a first flow channel and a second flow channel interconnected in fluid communication with one another,
   (b) said first flow channel structured to establish fluid flow between a patient and a monitoring device, said second flow channel structured and disposed to establish fluid flow between a supply of infusion fluid and said first flow channel,
   (c) flow regulator means movably mounted coaxially with said second flow channel for regulating flow of infusion fluid through said second flow channel to said first flow channel,
   (d) a continuous path of fluid flow and an intermittent path of fluid flow both disposed along a substantially common path of travel defined between an interior surface of said second flow channel and an outer surface of said flow regulator means,
   (e) said continuous path of fluid flow comprising a groove formed in said outer surface of said flow regulator means and said outer surface disposed in substantially mating engagement with said interior surface of said second flow channel along the length of said flow regulator means,
   (f) said intermittent path of fluid flow being of greater cross sectional dimension than said continuous path of fluid flow and defined by spaced apart, non-mating disposition of said interior and outer surfaces of said second flow channel and said flow regulator means respectively and along the length of said flow regulator means, and
   (g) whereby at least a minimal amount of fluid flow is maintained along said common path of travel independent of the position of said flow regulator means relative to said second flow channel.

2. A flow control device as in claim 1 wherein said groove comprises an elongated configuration extending along the length of said outer surface of said flow regulator, said groove means being dimensioned to provide a predetermined minimal continuous fluid flow therealong from said second flow channel to said first flow channel.

3. A flow control device as in claim 1 wherein said second flow channel comprises a substantially tapered configuration along the length thereof and said outer surface of said flow regulator means having a correspondingly tapered configuration with a substantially equal dimension relative to a first portion of the length of said interior surface of said second flow channel and a substantially lesser dimension than a second portion of the length thereof axially displaced from said first portion.

4. A flow control device as in claim 1 further comprising a fluid collecting cavity positioned within said housing common to both said first and said second flow channels and disposed in direct fluid receiving relation to both said continuous and intermittent paths of fluid flow, aperture means for establishing flow between said collecting cavity and said first flow channel and formed within said housing in contiguous, interconnecting relation between said collecting cavity and said first flow channel, wherein fluid flow being established through said housing by fluid passage from said second flow channel to said first flow channel successively passes through said collecting cavity and said aperture means.

5. A flow control device as in claim 1 wherein said flow regulator means comprises a plug element movably mounted within said second flow channel and positionable along the central longitudinal axis thereof between a closed and open position, said closed position defined by mating engagement between said plug element and the interior surface of said second flow channel, said closed position determining fluid flow through said continuous flow path exclusively and continuously in a predetermined small amount.

6. A flow control device as in claim 5 wherein said open position is defined by predetermined surface portions of said plug element including said groove disposed in spaced apart relation from said interior surface of said second flow channel, said open position determining fluid flow from said second flow channel to said first flow channel along said intermittent path, whereby fluid passes throughout the catheter system from said second flow channel.

7. A flow control device as in claim 5 wherein said plug element is reciprocally mounted on the interior of said second flow channel for selective reciprocal movement along the central longitudinal axis of said second flow channel, biasing means mounted on said plug element and interconnected between said plug element and said housing for normally biasing said plug element into said closed position and determining continuous fluid flow from said second flow channel, to said continuous path of fluid flow, to said first flow channel and the catheter system.

8. A flow control device as in claim 7 wherein said biasing means comprises a spring element formed of resilient material and interconnected between said plug element and said housing in biasing relation to said plug element, said spring element configured and disposed to cause displacement of said plug element into said open position upon force being applied thereto, whereby fluid flow is selectively directed through said second flow channel along said intermittent path upon application of the aforesaid force.

9. A flow control device as in claim 5 wherein said groove is integrally formed in said plug element and recessed inwardly from an outer surface portion thereof and in spaced relation to said interior surface of said second flow channel, said groove so disposed and structured and specifically dimensioned to establish continuous fluid communication along said second flow channel and a predetermined amount of fluid flow from said second flow channel to said first flow channel when said plug element is in said closed position.

* * * * *